(12) United States Patent
Short

(10) Patent No.: US 6,368,798 B1
(45) Date of Patent: Apr. 9, 2002

(54) SCREENING FOR NOVEL BIOACTIVITIES

(75) Inventor: Jay M. Short, Encinitas, CA (US)

(73) Assignee: Diversa Corporation, San Diego, CA (US)

( * ) Notice: Subject to any disclaimer, the term of this patent is extended or adjusted under 35 U.S.C. 154(b) by 0 days.

(21) Appl. No.: 09/421,970

(22) Filed: Oct. 20, 1999

Related U.S. Application Data

(60) Division of application No. 08/944,795, filed on Oct. 6, 1997, now Pat. No. 6,030,779, which is a continuation-in-part of application No. 08/692,002, filed on Aug. 2, 1996, now Pat. No. 6,054,267.
(60) Provisional application No. 60/008,317, filed on Dec. 7, 1995.

(51) Int. Cl.$^7$ ............................. C12Q 1/68; C12P 19/34
(52) U.S. Cl. ........................................... 435/6; 435/91.2
(58) Field of Search ............................. 435/6, 91.2, 7.1

(56) References Cited

U.S. PATENT DOCUMENTS 5,783,431 A * 7/1998 Peterson ........................ 435/6

FOREIGN PATENT DOCUMENTS

EP 285 123 * 10/1988

OTHER PUBLICATIONS

Maniatis Molecular Cloning, pp. 224–240, 270–274; 1982.*
Clontech Catalog, pp. 75, 91 1995.*
Short et al., Nucleic Acid Res. 16:7583–7600 1988.*
Hodgson Biotechnology 10:973–974; 1992.*
Osuna et al., Combinatorial mutagenesis of three major groove–contacting residues of EcoRI: single and double amino acid replacements retaining methyltransferase—sensitive, *Gene.* 1991, vol. 106, pp. 7–12.
Dube et al., Artificial mutants generated by the insertion of random oligonucleotides into the putative nucleoside binding site of the HSV–1 thymidine kinase gene, *Biochemistry*, 1991, vol. 30, pp. 11760–11767.
Burioni et al., Engineering human monoclonal antibody fragments: A recombinant enzyme–linked Fab. *Microbiologica.*, Apr. 1995, vol. 18, pp. 127–133.
Borrego et al., Combinatorial libraries by cassette mutagenesis, *Nucleic Acid Research,* 1995, vol. 23, No. 10, pp. 1834–1835.

* cited by examiner

*Primary Examiner*—Eggerton A. Campbell
(74) *Attorney, Agent, or Firm*—Gray Cary Ware & Freidenrich LLP; Lisa A. Haile

(57) ABSTRACT

Disclosed is a process for identifying clones having a specified enzyme activity by screening for the specified enzyme activity in a library of clones prepared by (i) selectively isolating target nucleic acid from nucleic acid derived from at least one microorganism, by use of at least one polynucleotide probe comprising at least a portion of a nucleic acid sequence encoding an enzyme having the specified enzyme activity; and (ii) transforming a host with isolated target nucleic acid to produce a library of clones which are screened for the specified enzyme activity.

50 Claims, 1 Drawing Sheet

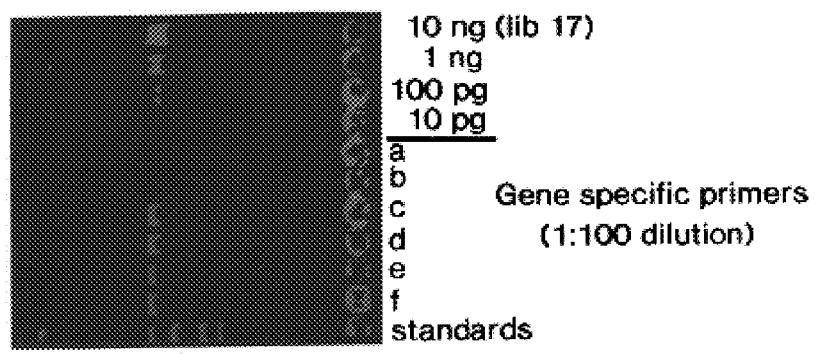
FIG. 1A
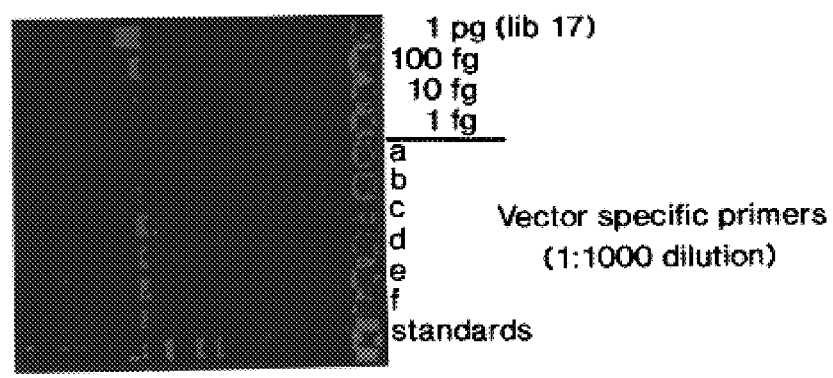
FIG. 1B
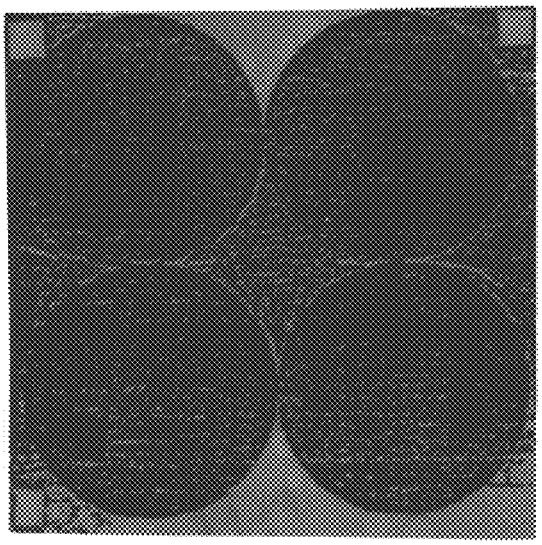
FIG. 2A  FIG. 2C
FIG. 2B  FIG. 2D

SCREENING FOR NOVEL BIOACTIVITIES

This application is a divisional application of U.S. patent application Ser. No. 08/944,795; filed on Oct. 6, 1997, now issued as U.S. Pat. No. 6,030,779, issued Feb. 29, 2000, which is a continuation-in-part of U.S. application Ser. No. 08/692,002, filed Aug. 2, 1996, issued Apr. 25, 2000 as U.S. Pat. No. 6,054,267, which claims priority under §119(e) to U.S. provisional application 60/008,317, filed Dec. 7, 1995, the contents of which are incorporated by reference in their entirety herein.

FIELD OF THE INVENTION

The present invention relates to the production and screening of expression libraries for enzyme activity and, more particularly, to obtaining selected polynucleotides from nucleic acid of a microorganism and to screening of an expression library for enzyme activity which is produced from selected polynucleotides.

BACKGROUND OF THE INVENTION

There is a critical need in the chemical industry for efficient catalysts for the practical synthesis of optically pure materials; enzymes can provide the optimal solution. All classes of molecules and compounds that are utilized in both established and emerging chemical, pharmaceutical, textile, food and feed, detergent markets must meet stringent economical and environmental standards. The synthesis of polymers, pharmaceuticals, natural products and agrochemicals is often hampered by expensive processes which produce harmful byproducts and which suffer from low enantioselectivity. Enzymes have a number of remarkable advantages which can overcome these problems in catalysis: they act on single functional groups, they distinguish between similar functional groups on a single molecule, and they distinguish between enantiomers. Moreover, they are biodegradable and function at very low mole fractions in reaction mixtures. Because of their chemo-, regio- and stereospecificity, enzymes present a unique opportunity to optimally achieve desired selective transformations. These are often extremely difficult to duplicate chemically, especially in single-step reactions. The elimination of the need for protection groups, selectivity, the ability to carry out multi-step transformations in a single reaction vessel, along with the concomitant reduction in environmental burden, has led to the increased demand for enzymes in chemical and pharmaceutical industries. Enzyme-based processes have been gradually replacing many conventional chemical-based methods. A current limitation to more widespread industrial use is primarily due to the relatively small number of commercially available enzymes. Only ~300 enzymes (excluding DNA modifying enzymes) are at present commercially available from the >3000 non DNA-modifying enzyme activities thus far described.

The use of enzymes for technological applications also may require performance under demanding industrial conditions. This includes activities in environments or on substrates for which the currently known arsenal of enzymes was not evolutionarily selected. Enzymes have evolved by selective pressure to perform very specific biological functions within the milieu of a living organism, under conditions of mild temperature, pH and salt concentration. For the most part, the non-DNA modifying enzyme activities thus far described have been isolated from mesophilic organisms, which represent a very small fraction of the available phylogenetic diversity. The dynamic field of biocatalysis takes on a new dimension with the help of enzymes isolated from microorganisms that thrive in extreme environments. Such enzymes must function at temperatures above 100° C. in terrestrial hot springs and deep sea thermal vents, at temperatures below 0° C. in arctic waters, in the saturated salt environment of the Dead Sea, at pH values around 0 in coal deposits and geothermal sulfur-rich springs, or at pH values greater than 11 in sewage sludge. Enzymes obtained from these extremophilic organisms open a new field in biocatalysis.

In addition to the need for new enzymes for industrial use, there has been a dramatic increase in the need for bioactive compounds with novel activities. This demand has arisen largely from changes in worldwide demographics coupled with the clear and increasing trend in the number of pathogenic organisms that are resistant to currently available antibiotics. For example, while there has been a surge in demand for antibacterial drugs in emerging nations with young populations, countries with aging populations, such as the U.S., require a growing repertoire of drugs against cancer, diabetes, arthritis and other debilitating conditions. The death rate from infectious diseases has increased 58% between 1980 and 1992 and it has been estimated that the emergence of antibiotic resistant microbes has added in excess of $30 billion annually to the cost of health care in the U.S. alone. (Adams et al., *Chemical and Engineering News*, 1995; Amann et al., *Microbiological Reviews*, 59, 1995). As a response to this trend pharmaceutical companies have significantly increased their screening of microbial diversity for compounds with unique activities or specificities.

There are several common sources of lead compounds (drug candidates), including natural product collections, synthetic chemical collections, and synthetic combinatorial chemical libraries, such as nucleotides, peptides, or other polymeric molecules. Each of these sources has advantages and disadvantages. The success of programs to screen these candidates depends largely on the number of compounds entering the programs, and pharmaceutical companies have to date screened hundred of thousands of synthetic and natural compounds in search of lead compounds. Unfortunately, the ratio of novel to previously-discovered compounds has diminished with time. The discovery rate of novel lead compounds has not kept pace with demand despite the best efforts of pharmaceutical companies. There exists a strong need for accessing new sources of potential drug candidates.

The majority of bioactive compounds currently in use are derived from soil microorganisms. Many microbes inhabiting soils and other complex ecological communities produce a variety of compounds that increase their ability to survive and proliferate. These compounds are generally thought to be nonessential for growth of the organism and are synthesized with the aid of genes involved in intermediary metabolism hence their name "secondary metabolites". Secondary metabolites that influence the growth or survival of other organisms are known as "bioactive" compounds and serve as key components of the chemical defense arsenal of both micro- and macroorganisms. Humans have exploited these compounds for use as antibiotics, antiinfectives and other bioactive compounds with activity against a broad range of prokaryotic and eukaryotic pathogens. Approximately 6,000 bioactive compounds of microbial origin have been characterized, with more than 60% produced by the gram positive soil bacteria of the genus Streptomyces. (Barnes et al., *Proc. Nat. Acad Sci. U.S.A.*, 91, 1994). Of these, at least 70 are currently used for biomedical and agricultural applications. The largest class of bioactive compounds, the polyketides, include a broad range of antibiotics, immunosuppressants and anticancer agents which together account for sales of over $5 billion per year.

Despite the seemingly large number of available bioactive compounds, it is clear that one of the greatest challenges facing modern biomedical science is the proliferation of antibiotic resistant pathogens. Because of their short generation time and ability to readily exchange genetic information, pathogenic microbes have rapidly evolved and disseminated resistance mechanisms against virtually all classes of antibiotic compounds. For example, there are virulent strains of the human pathogens Staphylococcus and Streptococcus that can now be treated with but a single antibiotic, vancomycin, and resistance to this compound will require only the transfer of a single gene, vana, from resistant Enterococcus species for this to occur. (Bateson et al., *System. Appl. Microbiol*, 12, 1989). When this crucial need for novel antibacterial compounds is superimposed on the growing demand for enzyme inhibitors, immunosuppressants and anti-cancer agents it becomes readily apparent why pharmaceutical companies have stepped up their screening of microbial diversity for bioactive compounds with novel properties.

SUMMARY OF THE INVENTION

The present invention provides a novel approach for obtaining enzymes for further use, for example, for a wide variety of industrial applications, for medical applications, for packaging into kits for use as research reagents and for other applications. In accordance with the present invention, recombinant enzymes are generated from microorganisms and are classified by various enzyme characteristics.

More particularly, one aspect of the present invention provides a process for identifying clones having a specified enzyme activity, which process comprises screening for said specified enzyme activity in a library of clones prepared by:

(i) selectively isolating target RNA or genomic DNA or fragments thereof, from nucleic acid derived from at least one microorganism, by use of at least one probe polynucleotide comprising at least a portion of a polynucleotide sequence encoding an enzyme having the specified enzyme activity; and (ii) transforming a host with isolated target cDNA, genomic DNA or fragments thereof, to produce a library of clones which are screened, preferably for the specified enzyme activity, using an activity library screening or nucleic acid library screening protocol.

In a preferred embodiment of this aspect, nucleic acid obtained from at least one microorganism is selected by recovering from the nucleic acid, polynucleotides which specifically bind, such as by hybridization, to a probe polynucleotide sequence. The nucleic acid obtained from the microorganism or microorganisms can be genomic DNA, RNA or genomic gene library DNA. One could even use nucleic acid prepared for vector ligation, for instance. The probe may be directly or indirectly bound to a solid phase by which it is separated from the nucleic acid which is not hybridized or otherwise specifically bound to the probe. The process can also include releasing nucleic acid from said probe after recovering said hybridized or otherwise bound nucleic acid and amplifying the nucleic acid so released.

The invention also provides for screening of the expression libraries for gene cluster protein product(s) and, more particularly, to obtaining selected gene clusters from nucleic acid of a prokaryote or eukaryote and to screening of an expression library for a desired activity of a protein of related activity(ies) of a family of proteins which results from expression of the selected gene cluster nucleic acid of interest.

More particularly, one embodiment of this aspect provides a process for identifying clones having a specified protein(s) activity, which process comprises screening for said specified enzyme activity in the library of clones prepared by (i) selectively isolating target gene cluster nucleic acid, from nucleic acid derived from at least one organism, by use of at least one probe polynucleotide comprising at least a portion of a polynucleotide sequence complementary to a nucleic acid sequence encoding the protein(s) having the specified activity of interest; and (ii) transforming a host with isolated target gene cluster nucleic acid to produce a library of such clones which are screened for the specified activity of interest. For example, if one is using DNA in a lambda vector one could package the DNA and infect cells via this route.

In a particular embodiment of this aspect, gene cluster nucleic acid obtained from the genomic nucleic acid of the organism(s) is selected by recovering from the nucleic acid, nucleic acid which specifically binds, such as by hybridization, to a probe polynucleotide sequence. The polynucleotide probe may be directly or indirectly bound to a solid phase by which it is separated from the nucleic acid which is not hybridized or otherwise specifically bound to the probe. This embodiment of this aspect of the process of the invention can also include releasing bound nucleic acid from said probe after recovering said hybridized or otherwise bound nucleic acid and amplifying the nucleic acid so released.

These and other aspects of the present invention will be apparent to those skilled in the art from the teachings herein.

BRIEF DESCRIPTION OF THE DRAWINGS

FIG. 1A shows a photograph of an agarose gel containing standards and samples a–f described in Example 2. Samples c–f represent DNA recovered from a genomic DNA library using two specific DNA probes and amplified using gene specific primers, as described in Example 2.

FIG. 1B shows a photograph of an agarose gel containing standards and samples a–f described in Example 2. Samples c–f represent DNA recovered from a genomic DNA library using two specific DNA probes and amplified using vector specific primers, as described in Example 2.

FIG. 2 shows a photograph of four colony hybridization plates. Plates A and B showed positive clones i.e., colonies which contained DNA prepared in accordance with the present invention, also contained probe sequence. Plates C and D were controls and showed no positive clones.

DETAILED DESCRIPTION OF THE INVENTION

Novel systems to clone and screen for enzymatic activities and bioactivities of interest in vitro are desirable. The method(s) of the present invention allow the cloning and discovery of novel bioactive molecules in vitro, and in particular novel bioactive molecules derived from uncultivated samples. Large size gene clusters, genes and gene fragments can be cloned and screened using the method(s) of the present invention. Unlike previous strategies, the method(s) of the present invention allow one to clone utilizing well known genetic systems, and to screen in vitro with crude (impure) preparations.

The present invention allows one to screen for and identify genes encoding enzymatic activities and bioactivities of interest from complex environmental gene expression libraries.

The microorganisms from which the libraries may be prepared include prokaryotic microorganisms, such as Eubacteria and Archaebacteria, and lower eukaryotic microorganisms such as fungi, some algae and protozoa. The microorganisms may be cultured microorganisms or uncultured microorganisms obtained from environmental samples and such microorganisms may be extremophiles, such as thermophiles, hyperthermophiles, psychrophiles and psychrotrophs.

As previously indicated, the library may be produced from environmental samples in which case nucleic acid may be recovered without culturing of an organism or the nucleic acid may be recovered from a cultured organism.

Sources of microorganism nucleic acid as a starting material library from which target nucleic acid is obtained are particularly contemplated to include environmental samples, such as microbial samples obtained from Arctic and Antarctic ice, water or permafrost sources, materials of volcanic origin, materials from soil or plant sources in tropical areas, etc. Thus, for example, nucleic acid may be recovered from either a culturable or non-culturable organism and employed to produce an appropriate recombinant expression library for subsequent determination of enzyme activity.

Bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. The gene cluster, the promoter, and additional sequences that function in regulation altogether are referred to as an "operon" and can include up to 20 or more genes, usually from 2 to 6 genes. Thus, a gene cluster is a group of adjacent genes that are either identical or related, usually as to their function.

Some gene families consist of identical members. Clustering is a prerequisite for maintaining identity between genes, although clustered genes are not necessarily identical. Gene clusters range from extremes where a duplication is generated to adjacent related genes to cases where hundreds of identical genes lie in a tandem array. Sometimes no significance is discernable in a repetition of a particular gene. A principal example of this is the expressed duplicate insulin genes in some species, whereas a single insulin gene is adequate in other mammalian species.

It is important to further research gene clusters and the extent to which the full length of the cluster is necessary for the expression of the proteins resulting therefrom. Further, gene clusters undergo continual reorganization and, thus, the ability to create heterogeneous libraries of gene clusters from, for example, bacterial or other prokaryote sources is valuable in determining sources of novel proteins, particularly including enzymes such as, for example, the polyketide synthases that are responsible for the synthesis of polyketides having a vast array of useful activities. Other types of proteins that are the product(s) of gene clusters are also contemplated, including, for example, antibiotics, antivirals, antitumor agents and regulatory proteins, such as insulin.

Polyketides are molecules which are an extremely rich source of bioactivities, including antibiotics (such as tetracyclines and erythromycin), anti-cancer agents (daunomycin), immunosuppressants (FK506 and rapamycin), and veterinary products (monensin). Many polyketides (produced by polyketide synthases) are valuable as therapeutic agents. Polyketide synthases are multifunctional enzymes that catalyze the biosynthesis of a hugh variety of carbon chains differing in length and patterns of functionality and cyclization. Polyketide synthase genes fall into gene clusters and at least one type (designated type I) of polyketide synthases have large size genes and enzymes, complicating genetic manipulation and in vitro studies of these genes/proteins.

The ability to select and combine desired components from a library of polyketides and postpolyketide biosynthesis genes for generation of novel polyketides for study is appealing. The method(s) of the present invention make it possible to and facilitate the cloning of novel polyketide synthases, since one can generate gene banks with clones containing large inserts (especially when using the f-factor based vectors), which facilitates cloning of gene clusters.

Preferably, the gene cluster nucleic acid is ligated into a vector, particularly wherein a vector further comprises expression regulatory sequences which can control and regulate the production of a detectable protein or protein-related array activity from the ligated gene clusters. Use of vectors which have an exceptionally large capacity for exogenous nucleic acid introduction are particularly appropriate for use with such gene clusters and are described by way of example herein to include the f-factor (or fertility factor) of E. coli. This f-factor of E. coli is a plasmid which affect high-frequency transfer of itself during conjugation and is ideal to achieve and stably propagate large nucleic acid fragments, such as gene clusters from mixed microbial samples.

The term "isolated" means that material is removed from its original environment (e.g., the natural environment if it is naturally occurring). For example, a naturally-occurring polynucleotide or polypeptide present in a living animal is not isolated, but the same polynucleotide or polypeptide separated from some or all of the coexisting materials in the natural system, is isolated.

The nucleic acid isolated or derived from these microorganisms can preferably be inserted into a vector or a plasmid prior to probing for selected polynucleotides. Such vectors or plasmids are preferably those containing expression regulatory sequences, including promoters, enhancers and the like. Such polynucleotides can be part of a vector and/or a composition and still be isolated, in that such vector or composition is not part of its natural environment. Particularly preferred phage or plasmid and methods for introduction and packaging into them are described in detail in the protocol set forth herein.

The following outlines a general procedure for producing libraries from both culturable and non-culturable organisms, which libraries can be probed to select therefrom nucleic acid sequences which hybridize to specified probe polynucleotides:

ENVIRONMENTAL SAMPLE

Obtain Biomass
nucleic acid Isolation (various methods for DNA and RNA isolation)
For Example:
Shear DNA (25 gauge needle)
Blunt DNA (Mung Bean Nuclease)
Methylate DNA (EcoR I Methylase)
Ligate to EcoR I linkers (GGAATTCC)
Cut back linkers (EcoR I Restriction Endonuclease)
Size Fractionate (Sucrose Gradient)
Ligate to lambda vector Package (in vitro lambda packaging extract)
Plate on *E. coli* host and amplify The probe polynucleotide used for selectively isolating the target nucleic acid of interest from the nucleic acid derived from at least one microorganism can be a full-length coding region sequence or a partial coding region sequence of nucleic acid for an enzyme of known activity. The original nucleic acid library can be preferably probed using mixtures of probes comprising at least a portion of nucleic acid sequences encoding enzymes having the specified enzyme activity. These probes or probe libraries are preferably single-stranded and the microbial nucleic acid which is probed has preferably been converted into single-stranded form. The probes that are particularly suitable are those derived from nucleic acid encoding enzymes having an activity similar or identical to the specified enzyme activity which is to be screened.

The probe polynucleotide should be at least about 10 bases and preferably at least 15 bases. In one embodiment, the entire coding region may be employed as a probe. Conditions for the hybridization in which target nucleic acid is selectively isolated by the use of at least one polynucleotide probe will be designed to provide a hybridization stringency of at least about 50% sequence identity, more particularly a stringency providing for a sequence identity of at least about 70%.

Hybridization techniques for probing a microbial nucleic acid library to isolate target nucleic acid of potential interest are well known in the art and any of those which are described in the literature are suitable for use herein to probe nucleic acid for separation from the remainder of the nucleic acid derived from the microorganisms. Solution phase hybridizations followed by binding of the probe to a solid phase is preferable.

Preferably the probe polynucleotide is "labeled" with one partner of a specific binding pair (i.e. a ligand) and the other partner of the pair is bound to a solid matrix to provide ease of separation of target from its source. The ligand and specific binding partner can be selected from, in either orientation, the following: (1) an antigen or hapten and an antibody or specific binding fragment thereof; (2) biotin or iminobiotin and avidin or streptavidin; (3) a sugar and a lectin specific therefor; (4) an enzyme and an inhibitor therefor; (5) an apoenzyme and cofactor; (6) complementary homopolymeric oligonucleotides; and (7) a hormone and a receptor therefor. The solid phase is preferably selected from: (1) a glass or polymeric surface; (2) a packed column of polymeric beads; and (3) magnetic or paramagnetic particles.

Further, it is optional but desirable to perform an amplification of the target nucleic acid that has been isolated. In this embodiment the target nucleic acid is separated from the probe polynucleotide after isolation. It is then amplified before being used to transform hosts. The double stranded nucleic acid selected to include as at least a portion thereof a predetermined nucleic acid sequence can be rendered single stranded, subjected to amplification and reannealed to provide amplified numbers of selected double stranded nucleic acid. Numerous amplification methodologies are now well known in the art.

The selected nucleic acid is then used for preparing a library for screening by transforming a suitable organism. Hosts, particularly those specifically identified herein as preferred, are transformed by artificial introduction of the vectors containing the target nucleic acid by inoculation under conditions conducive for such transformation. One could transform with double stranded circular or linear nucleic acid or there may also be instances where one would transform with single stranded circular or linear nucleic acid.

The resultant libraries of transformed clones are then screened for clones which display activity for the enzyme of interest in a phenotypic assay for enzyme activity.

Having prepared a multiplicity of clones from nucleic acid selectively isolated from an organism, such clones are screened for a specific enzyme activity and to identify the clones having the specified enzyme characteristics.

The screening for enzyme activity may be effected on individual expression clones or may be initially effected on a mixture of expression clones to ascertain whether or not the mixture has one or more specified enzyme activities. If the mixture has a specified enzyme activity, then the individual clones may be rescreened for such enzyme activity or for a more specific activity. Thus, for example, if a clone mixture has hydrolase activity, then the individual clones may be recovered and screened to determine which of such clones has hydrolase activity.

As described with respect to one of the above aspects, the invention provides a process for enzyme activity screening of clones containing selected nucleic acid derived from a microorganism which process comprises:

screening a library for specified enzyme activity, said library including a plurality of clones, said clones having been prepared by recovering from nucleic acid of a microorganism selected nucleic acid, which nucleic acid is selected by hybridization to at least one nucleic acid sequence which is all or a portion of a nucleic acid sequence encoding an enzyme having the specified activity; and transforming a host with the selected nucleic acid to produce clones which are screened for the specified enzyme activity.

In one embodiment, a nucleic acid library derived from a microorganism is subjected to a selection procedure to select therefrom nucleic acid which hybridizes to one or more probe nucleic acid sequences which is all or a portion of a nucleic acid sequence encoding an enzyme having the specified enzyme activity by:

(a) rendering the double-stranded nucleic acid population into a single-stranded nucleic acid population;

(b) contacting the single-stranded nucleic acid population of (a) with the nucleic acid probe bound to a ligand under conditions permissive of hybridization so as to produce a double-stranded complex of probe and members of the nucleic acid population which hybridize thereto;

(c) contacting the double-stranded complex of (b) with a solid phase specific binding partner for said ligand so as to produce a solid phase complex;

(d) separating the solid phase complex from the single-stranded nucleic acid population of (b);

(e) releasing from the probe the members of the population which had bound to the solid phase bound probe;

(f) forming double-stranded nucleic acid from the members of the population of (e);

(g) introducing the double-stranded nucleic acid of (f) into a suitable host to form a library containing a plurality of clones containing the selected nucleic acid; and (h) screening the library for the specified enzyme activity.

In another embodiment, a nucleic acid library derived from a microorganism is subjected to a selection procedure to select therefrom double-stranded nucleic acid which hybridizes to one or more probe polynucleotide sequences which is all or a portion of a nucleic acid sequence encoding an enzyme having the specified enzyme activity by:

(a) contacting the double-stranded nucleic acid population with the polynucleotide probe bound to a ligand under conditions permissive of hybridization so as to produce a complex of probe and members of the nucleic acid population which hybridize thereto;

(b) contacting the complex of (a) with a solid phase specific binding partner for said ligand so as to produce a solid phase complex;

(c) separating the solid phase complex from the unbound nucleic acid population of (b);

(d) releasing from the probe the members of the population which had bound to the solid phase bound probe;

(e) introducing the double-stranded nucleic acid of (d) into a suitable host to form a library containing a plurality of clones containing the selected nucleic acid; and (f) screening the library for the specified enzyme activity.

In another aspect, the process includes a preselection to recover nucleic acid including signal or secretion sequences. In this manner it is possible to select from the nucleic acid population by hybridization as herein above described only nucleic acid which includes a signal or secretion sequence. The following paragraphs describe the protocol for this embodiment of the invention, the nature and function of secretion signal sequences in general and a specific exemplary application of such sequences to an assay or selection process.

Another particularly preferred embodiment of this aspect further comprises, after (a) but before (a) above, the steps of:

(i). contacting the double-stranded nucleic acid population of (a) with a ligand-bound oligonucleotide probe that is complementary to a secretion signal sequence unique to a given class of proteins under conditions permissive of hybridization to form a double-stranded complex;

(ii). contacting the complex of (a i) with a solid phase specific binding partner for said ligand so as to produce a solid phase complex;

(iii) separating the solid phase complex from the unbound nucleic acid population;

(iv) releasing the members of the population which had bound to said solid phase bound probe; and (v) separating the solid phase bound probe from the members of the population which had bound thereto.

The nucleic acid which has been selected and isolated to include a signal sequence is then subjected to the selection procedure herein above described to select and isolate therefrom nucleic acid which binds to one or more probe nucleic acid sequences derived from nucleic acid encoding an enzyme(s) having the specified enzyme activity.

The pathways by which proteins are sorted and transported to their proper cellular location are often referred to as protein targeting pathways. One of the most important elements in all of these targeting systems is a short amino acid sequence at the amino terminus of a newly synthesized polypeptide called the signal sequence. This signal sequence directs a protein to its appropriate location in the cell and is removed during transport or when the protein reaches its final destination. Most lysosomal, membrane, or secreted proteins have an amino-terminal signal sequence that marks them for translocation into the lumen of the endoplasmic reticulum. More than 100 signal sequences for proteins in this group have been determined. The sequences vary in length from 13 to 36 amino acid residues.

A phoA expression vector, termed pMG, which, like TaphoA, is useful in identifying genes encoding membrane-spanning sequences or signal peptides. Giladi et al., J. Bacteriol., 175(13):4129–4136, 1993. This cloning system has been modified to facilitate the distinction of outer membrane and periplasmic alkaline phosphatase (AP) fusion proteins from inner membrane AP fusion proteins by transforming pMG recombinants into $E.$ $coli$ KS330, the strain utilized in the "blue halo" assay first described by Strauch and Beckwith, Proc. Nat. Acad. Sci. USA, 85:1576–1580, 1988. The pMG/KS330r$^-$ cloning and screening approach can identify genes encoding proteins with clevable signal peptides and therefore can serve as a first step in the identification of genes encoding polypeptides of interest.

The nucleic acid derived from a microorganism(s) is preferably inserted into an appropriate vector (generally a vector containing suitable regulatory sequences for effecting expression) prior to subjecting such nucleic acid to a selection procedure to select and isolate therefrom nucleic acid which hybridizes to nucleic acid derived from nucleic acid encoding an enzyme(s) having the specified enzyme activity.

As representative examples of expression vectors which may be used there may be mentioned viral particles, baculovirus, phage, plasmids, phagemids, cosmids, phosmids, bacterial artificial chromosomes, viral nucleic acid (e.g. vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, aspergillus, yeast, etc.) Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE70, pQE60, pQE-9 (Qiagen), psiX174, pBluescript SK, pBluescript KS, pNH8A, pNH16a, pNH18A, pNH46A (Stratagene); pTRC99a, pKK223-3, pKK233-3, pDR540, pRIT5 (Pharmacia); Eukaryotic: pWLNEO, pSV2CAT, pOG44, pXT1, pSG (Stratagene), pSVK3, pBPV, pMSG, pSVL (Pharmacia). However, any other plasmid or vector may be used as long as they are replicable and viable in the host.

A particularly preferred type of vector for use in the present invention contains an f-factor origin replication. The f-factor (or fertility factor) in $E.$ $coli$ is a plasmid which effects high frequency transfer of itself during conjugation and less frequent transfer of the bacterial chromosome itself. A particularly preferred embodiment is to use cloning vectors, referred to as "fosmids" or bacterial artificial chromosome (BAC) vectors. These are derived from $E.$ $coli$ f-factor which is able to stably integrate large segments of DNA. When integrated with DNA from a mixed uncultured environmental sample, this makes it possible to achieve large genomic fragments in the form of a stable "environmental DNA library."

The nucleic acid derived from a microorganism(s) may be inserted into the vector by a variety of procedures. In general, the nucleic acid sequence is inserted into an appropriate restriction endonuclease site(s) by procedures known in the art. Such procedures and others are deemed to be within the scope of those skilled in the art.

The nucleic acid sequence in the expression vector is operatively linked to an appropriate expression control sequence(s) (promoter) to direct mRNA synthesis. Particular named bacterial promoters include laci, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium.

The nucleic acid selected and isolated as herein above described is introduced into a suitable host to prepare a library which is screened for the desired enzyme activity. The selected nucleic acid is preferably already in a vector which includes appropriate control sequences whereby selected nucleic acid which encodes for an enzyme may be expressed, for detection of the desired activity. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

As representative examples of appropriate hosts, there may be mentioned: bacterial cells, such as *E. coli*, Streptornyces, *Salmonella typhimurium*; fungal cells, such as yeast; insect cells such as Drosophila S2 and Spodoptera SJ9; animal cells such as CHO, COS or Bowes melanoma; adenoviruses; plant cells, etc. The selection of an appropriate host is deemed to be within the scope of those skilled in the art from the teachings herein.

With particular references to various mammalian cell culture systems that can be employed to express recombinant protein, examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. nucleic acid sequences derived from the SV40 splice, and polyadenylation sites may be used to provide the required nontranscribed genetic elements.

Host cells are genetically engineered (transduced or transformed or transfected) with the vectors. The engineered host cells can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan.

The library may be screened for a specified enzyme activity by procedures known in the art. For example, the enzyme activity may be screened for one or more of the six IUB classes; oxidoreductases, transferases, hydrolases, lyases, isomerases and ligases. The recombinant enzymes which are determined to be positive for one or more of the IUB classes may then be rescreened for a more specific enzyme activity.

Alternatively, the library may be screened for a more specialized enzyme activity. For example, instead of generically screening for hydrolase activity, the library may be screened for a more specialized activity, i.e. the type of bond on which the hydrolase acts. Thus, for example, the library may be screened to ascertain those hydrolases which act on one or more specified chemical functionalities, such as: (a) amide (peptide bonds), i.e. proteases; (b) ester bonds, i.e. esterases and lipases; (c) acetals, i.e., glycosidases.

The clones which are identified as having the specified enzyme activity may then be sequenced to identify the nucleic acid sequence encoding an enzyme having the specified activity. Thus, in accordance with the present invention it is possible to isolate and identify: (i) nucleic acid encoding an enzyme having a specified enzyme activity, (ii) enzymes having such activity (including the amino acid sequence thereof) and (iii) produce recombinant enzymes having such activity.

Having thus disclosed exemplary embodiments of the present invention, it should be noted by those skilled in the art that the disclosures are exemplary only and that various other alternatives, adaptations and modifications may be made within the scope of the present invention. Accordingly, the present invention is not limited to the specific embodiments as illustrated herein.

Without further elaboration, it is believed that one skilled in the art can, using the preceding description, utilize the present invention to its fullest extent. The following examples are to be considered illustrative and thus are not limiting of the remainder of the disclosure in any way whatsoever.

Example 1

Examples of Enzymes which can be Identified by the Invention

Lipase/Esterase
  a. Enantioselective hydrolysis of esters (lipids)/thioesters
     1) Resolution of racemic mixtures
     2) Synthesis of optically active acids or alcohols from meso-diesters
  b. Selective syntheses
     1) Regiospecific hydrolysis of carbohydrate esters
     2) Selective hydrolysis of cyclic secondary alcohols
  c. Synthesis of optically active esters, lactones, acids, alcohols
     1) Transesterification of activated/nonactivated esters
     2) Interesterification
     3) Optically active lactones from hydroxyesters
     4) Regio- and enantioselective ring opening of anhydrides d. Detergents
  e. Fat/Oil conversion
  f. Cheese ripening
2 Protease
  a. Ester/amide synthesis
  b. Peptide synthesis
  c. Resolution of racemic mixtures of amino acid esters
  d. Synthesis of non-natural amino acids
  e. Detergents/protein hydrolysis
3 Glycosidase/Glycosyl transferase
  a. Sugar/polymer synthesis
  b. Cleavage of glycosidic linkages to form mono, di- and oligosaccharides
  c. Synthesis of complex oligosaccharides
  d. Glycoside synthesis using UDP-galactosyl transferase
  e. Transglycosylation of disaccharides, glycosyl fluorides, aryl galactosides
  f. Glycosyl transfer in oligosaccharide synthesis
  g. Diastereoselective cleavage of β-glucosylsulfoxides
  h. Asymmetric glycosylations
  i. Food processing
  j. Paper processing
4 Phosphatase/Kinase
  a. Synthesis/hydrolysis of phosphate esters
    1) Regio-, enantioselective phosphorylation
    2) Introduction of phosphate esters
    3) Synthesize phospholipid precursors
    4) Controlled polynucleotide synthesis
  b. Activate biological molecule
  c. Selective phosphate bond formation without protecting groups
Mono/Dioxygenase
  a. Direct oxyfunctionalization of unactivated organic substrates
  b. Hydroxylation of alkane, aromatics, steroids
  c. Epoxidation of alkenes
  d. Enantioselective sulphoxidation
  e. Regio- and stereoselective Bayer-Villiger oxidations
6 Haloperoxidase
  a. Oxidative addition of halide ion to nucleophilic sites
  b. Addition of hypohalous acids to olefinic bonds
  c. Ring cleavage of cyclopropanes
  d. Activated aromatic substrates converted to ortho and para derivatives
  e. 1.3 diketones converted to 2-halo-derivatives
  f. Heteroatom oxidation of sulfur and nitrogen containing substrates
  g. Oxidation of enol acetates, alkynes and activated aromatic rings
7 Lignin peroxidase/Diarylpropane peroxidase
  a. Oxidative cleavage of C—C bonds
  b. Oxidation of benzylic alcohols to aldehydes
  c. Hydroxylation of benzylic carbons
  d. Phenol dimerization
  e. Hydroxylation of double bonds to form diols
  f. Cleavage of lignin aldehydes
Epoxide hydrolase
  a. Synthesis of enantiomerically pure bioactive compounds
  b. Regio- and enantioselective hydrolysis of epoxide
  c. Aromatic and olefinic epoxidation by monooxygenases to form epoxides
  d. Resolution of racemic epoxides
  e. Hydrolysis of steroid epoxides
9 Nitrile hydratase/nitrilase
  a. Hydrolysis of aliphatic nitriles to carboxamides
  b. Hydrolysis of aromatic, heterocyclic, unsaturated aliphatic nitriles to corresponding acids
  c. Hydrolysis of acrylonitrile
  d. Production of aromatic and carboxamides, carboxylic acids (nicotinamide, picolinamide, isonicotinamide)
  e. Regioselective hydrolysis of acrylic dinitrile
  f. α-amino acids from α-hydroxynitriles
10 Transaminase
  a. Transfer of amino groups into oxo-acids
11 Amidase/Acylase
  a. Hydrolysis of amides, amidines, and other C—N bonds
  b. Non-natural amino acid resolution and synthesis Example 2

Preparation of a Genomic DNA Library in Lambda ZAPII

Cloning DNA fragments prepared by random cleavage of the target DNA generates the most representative library. An aliquot of DNA (50–100 μg) isolated from biomass is prepared as follows:

The DNA is sheared by vigorous passage through a 25 gauge double-hub needle attached to 1-ml syringes. An aliquot (0.5 μg) is electrophoresed through a 0.8% agarose gel to confirm that the majority of the sheared DNA is within the desired size range (3–6 kb).

The sheared DNA is "polished" or made blunt-ended by treatment with mung bean nuclease. First, the sheared DNA is brought up to a volume of 405 μl with Tris/EDTA (TE buffer) and incubated with 10×mung bean buffer (45 μl) and mung bean nuclease (2.0 μl, 150 U/μl) for 15 minutes at 37° C. The reaction is extracted once with phenol/chloroform and then once with chloroform alone. The DNA is precipitated by adding ice-cold ethanol (1 ml) and is placed on ice for 10 minutes. The precipitate is spun in a microcentrifuge (high speed, 30 minutes), washed with 70% ethanol (1 ml), microcentrifuged again (high speed, 10 minutes), dried and resuspended in TE buffer (26 μl).

EcoR I sites in the DNA must be protected from future enzymatic reactions. To accomplish this, the DNA is incubated with 10×EcoR I methylase (5.0 μl, 40 U/μl) for 1 hour at 37° C.

The DNA is further treated to ensure that it is blunt-ended by incubation with 100 mM MgCl$_2$ (5.0 μl), dNTP mix (8.0 μl, 2.5 mM of each dGTP, dATP, dCTP, dTTP) and DNA polymerase I large (Klenow) fragment (4.0 μl, 5 U/μl) for 30 minutes at 12° C. Then, 1×sodium chloride/Tris/EDTA (STE buffer) 450 μl) is added and the reaction is extracted once with phenol/chloroform and then once with chloroform alone. The DNA is precipitated by adding ice-cold ethanol (1 ml) and is placed on ice for 10 minutes. The precipitate is spun in a microcentrifuge (high speed, 30 minutes), washed with 70% ethanol (1 ml), microcentrifuged again (high speed, 10 minutes), dried and resuspended in TE buffer (7.0 μl).

The blunt-ended DNA is made compatible with the vector cloning site by ligating to EcoR I linkers using a very high molar ratio of linkers to DNA. This lowers the probability of two DNA molecules ligating together creating a chimeric clone and increases the probability of linkers ligating to both ends of the DNA molecules. The ligation reaction is performed by adding EcoR I linkers [GGAATTCC] (14 µl, 200 ng/µl), 10×ligase buffer (3.0 µl), 10 mM rATP (3.0 µl) and T4 DNA ligase (3.0 µl, 4 WU/µl) and incubating at 4° C. overnight.

The ligation reaction is terminated by heating to 68° C. for 10 minutes. The linkers are digested to create EcoR I overhangs by incubation with water (238 µl), 10×EcoR I buffer (30 µl) and EcoR I restriction endonuclease (2.0 µl, 100 U/µl) for 1.5 hours at 37° C. The digestion reaction is discontinued by adding 0.5 M EDTA and the DNA is placed on ice.

The DNA is size fractionated through a sucrose gradient which is rapid, reliable and relatively free of inhibiting contaminants. The removal of sub-optimal DNA fragments and the small linkers is critical because ligation to the vector can result in recombinant molecules that are too large and unpackageable by in viro lambda packaging extracts or can result in the construction of a "linker library." The DNA sample is heated to 65° C. for 10 minutes and loaded on a 10-ml sucrose gradient (40% w/v). The gradient is spun in an ultracentrifuge at room temperature, 25K for 16 hours. Fractions are collected from the gradient by puncturing the bottom of the gradient tube with an 18 gauge needle and collecting the sucrose solution which flows through the needle (10 drops per fraction). A small aliquot (20 µl) of each fraction is analyzed by 0.8% agarose gel electrophoresis and the fractions containing DNA in the desired size range (3–6 kb) is precipitated by adding ice cold ethanol (1 ml). The precipitate is spun in a microcentrifuge (high speed, 30 minutes), washed with 70% ethanol (1 ml), microcentrifuged again (high speed, 10 minutes), dried and resuspended in TE buffer (5–10 µl).

A plate assay is performed on the resuspended DNA to acquire an approximate concentration by spotting 0.5 µl of the DNA on 0.8% agarose containing ehtidium bromide (5 µg/ml). The DNA is visually compared to spotted DNA standards of known concentration by viewing on a UV light box.

The DNA is ligated to Lambda ZAP II cloning vector arms which were digested with EcoR I restriction enzyme and dephosphorylated. The ligation reaction has a final volume of 5.0 µl and contains 10×ligase buffer (0.5 µl), 10 mM rATP (0.5 µl), Lambda ZAP II arms (1.0 µl, 1.0 µg/µl), DNA ($\leq$2.5 µl, 200 ng), T4 DNA ligase (0.5 µl, 4 WU/µl) and water (as needed to bring the final volume up to 5.0 µl). The ligation reaction is incubated overnight at 4° C.

The ligation reaction is packaged using two in vitro lambda packaging extracts (2.5 µl of ligation per extract) in accordance with the manufacturer's protocol. The packaging reactions are stopped with the addition of sodium chloride/MgSO$_4$/Tris/gelatin (SM buffer) (500 µl) and pooled for a total volume of 1 ml per ligation reaction. The packaged phage are titrated on a suitable host, for example, XL1-Blue MRF' E. coli cells, as follows:

Host cells (200 µl, OD$_{600}$=1.0 in MgSO$_4$) are aliquotted into tubes, inoculated with the packaged phage (1 µl) and incubated for 15 minutes at 37° C. Top agar (3 ml, 48° C.) containing Isopropyl-β-D-thio-galactopyranoside (IPTG) (1.5 mM) and 5-bromo-4-chloro-3-indoyl-β-D-galactopyranoside (X-gal) (2.5 mg/ml) is added to each tube, plated onto 100-mm petri dishes containing bottom agar and incubated at 37° C. overnight. The number of plaque forming units (pfu) are calculated as follows. Typical results are $5.0\times10^5$–$1.0\times10^6$ pfu/ml with a 5% background (nonrecombinants).

(# clear pfu)×(1,000 µl packaged phage)=#recombinant pfu/ml

A portion of the library ($\leq$2.5×10$^5$ pfu) is amplified as follows. Host cells (3 ml, OD$_{600}$=1.0 in MgSO$_4$) are aliquotted into 50-ml conical tubes, inoculated with packaged phage ($\leq$2.5×10$^5$ pfu) and incubated for 20 minutes at 37° C. Top agar (40 ml, 48° C.) is added to each tube and plated across five 150-mm petri dishes containing bottom agar and incubated at 37° C. for 6–8 hours or until plaques are about pinhead in size.

The phage particles are harvested by overlaying the plates with SM buffer (8–10 ml) and maintaining the plates at 4° C. overnight with gentle rocking. The phage elute into the SM buffer and are recovered by pouring the SM buffer off of each plate into a 50-ml conical tube. Chloroform (3 ml) is added to each tube which is then shaken vigorously, incubated at room temperature for 15 minutes and centrifuged (2,000 rpm, 10 minutes) to remove cell debris. The supernatant (amplified library) is then decanted into a fresh 50-ml conical tube to which chloroform (500 µl) is added and stored at 4° C. for later use.

The amplified library is titered as follows. Serial dilutions of the amplified library are preapred in SM buffer (10$^{-5}$, 10$^{-6}$). Host cells (200 µl, OD$_{600}$=1.0 in MgSO$_4$) are aliquotted into two tubes, inoculated with the diluted phage (1 µl from each dilution) and incubated for 15 minutes at 37° C. Top agar (3 ml, 48° C.) containing Isopropyl-β-D-thio-galactopyranoside (IPTG) (1.5 mM) and 5-bromo4-chloro-3-indoyl-β-D-galactopyranoside (X-gal) (2.5 mg/ml) is added to each tube, plated onto 100-mm petri dishes containing bottom agar and incubated at 37° C. overnight. The number of plaque forming units are calculated. Typical results are 1.0×10$^{10}$ pfu/ml with a 5% background (nonrecombinants).

Example 3

Hybridization Selection and Production of Expression Library

Starting with a plasmid library prepared as described in Example 1, hybridization selection and preparation of the expression library were performed according to the protocol described in this example. The library can contain DNA from isolated microorganisms, enriched cultures or environmental samples.

Single-stranded DNA is made in one of two ways: 1) The plasmid library can be grown and the double-stranded plasmid DNA isolated. The double-stranded DNA is made single-stranded using F1 gene I protein and Exonuclease III. The gene II protein nicks the double-stranded plasmids at the F1 origin and the Exo III digests away the nicked strand leaving a single-stranded circle. This method is used by Life Technologies in their GeneTrapper™ kit; 2) the second method involves the use of a helper phage to "rescue" one of the strands of the double-stranded plasmids. The plasmid library is grown in a small overnight culture. A small aliquot of this is mixed with VCS-M13 helper phage and again grown overnight. The next morning the phagemids (virus particles containing single-stranded DNA) are recovered from the media and used in the following protocol.

PROTOCOL

1. Six samples of 4 µg of rescued, single-stranded DNA from library #17 were prepared in 3×SSC buffer. Final reaction volumes were 30 µl.

2. To these solutions was added one of the following:
   a) nothing
   b) 100 ng of biotinylated probe from an unrelated sequence
   c,d) 100 ng of biotinylated probe from organism #13 DNA polymerase gene
   e,f) 100 ng of biotinylated probe from organism #17 DNA polymerase gene Biotinylated probes were prepared by PCR amplification of fragments of ~1300 bp in length coding for a portion of the DNA polymerase gene of these organisms. The amplification products were made using biotinylated dUTP in the amplification mix. This modified nucleotide is incorporated throughout the DNA during synthesis. Unincorporated nucleotides were removed using the QIAGEN PCR Clean-up kit.
3. These mixtures were denatured by heating to 95° C. for 2 minutes.
4. Hybridization was performed for 90 minutes at 70° C. for samples a, b, d and f. Samples c and e were hybridized at 60° C.
5. 50 µl of washed and blocked MPG beads were added and mixed to each sample. These mixtures were agitated every 5 minutes for a total of 30 minutes. MPG beads are sent at 1 mg/ml in buffer containing preservative so 6 sets of 100 µl were washed 2 times in 3×SSC and resuspended in 60 µl of 3×SSC containing 100 µg of sonicated salmon sperm DNA.
6. The DNA/bead mixtures were washed 2 times at room temperature in 0.1×SSC/0.1% SDS, 2 times at 42° C. in 0.1×SSC/0.1% SDS for 10 minutes each and 1 additional wash at room temperature with 3×SSC.
7. The bound DNA was eluted by heating the beads to 70° C. for 15 minutes in 50 µl TE.
8. Dilutions of the eluted DNAs were made and PCR amplification was performed with either gene specific primers or vectors specific primers. Dilutions of the library DNA were used as standards.
9. The DNA inserts contained within the DNA were amplified by PCR using vector specific primers. These inserts were cloned using the TA Cloning system (Invitrogen).
10. Duplicates of 92 white colonies and 4 blue colonies from samples d and f were grown overnight and colony lifts were prepared for Southern blotting.
11. The digoxigenin system from Boehringer Mannheim was used to probe the colonies using the organism #17 probe.

RESULTS

PCR Quantitation

FIGS. 1A and 1B. FIG. 1A is a photograph of the autoradiogram resulting from the Southern hybridization agarose gel electrophoresis columns of DNA from sample solutions a–f in Example 2, when hybridized with gene specific primers. FIG. 1B is a photograph of the autoradiogram resulting from the Southern hybridization agarose gel electrophoresis columns of DNA from sample solutions a–f in Example 2, when hybridized with vector specific primers.

The gene specific DNA amplifications of samples a and b demonstrate that non-specific binding to the beads is minimal. The amount of DNA bound under the other conditions results in the following estimates of enrichment.

|   | gene specific equivalent | total  | enrichment |
|---|---|---|---|
| c | 50 ng | 100 pg | 500X |
| d | 50 ng | 30 pg  | 1667X |
| e | 20 ng | 50 pg  | 400 |
| f | 20 ng | 20 pg  | 1000X |

Colony Hybridization

FIG. 2 is a photograph of four colony hybridization plates resulting from Plates A and B show positive clones i.e., colonies containing sequences contained in the probe and which contain DNA from a library prepared in accordance with the invention. Plates C and D were controls and showed no positive clones.

Seven of 92 colonies from the panned sample were positive for sequences contained in the probe. No positive clones were found in the unpanned sample.

Example 4

Construction of a Stable, Large Insert DNA Library of Picoplankton Genomic DNA

Cell collection and preparation of DNA. Agarose plugs containing concentrated picoplankton cells were prepared from samples collected on an oceanographic cruise from Newport, Oregon to Honolulu, Hawaii. Seawater (30 liters) was collected in Niskin bottles, screened through 10 µm Nitex, and concentrated by hollow fiber filtration (Amicon DC10) through 30,000 MW cutoff polyfulfone filters. The concentrated bacterioplankton cells were collected on a 0.22 µm, 47 mm Durapore filter, and resuspended in 1 ml of 2×STE buffer (1M NaCl, 0.1M EDTA, 10 mM Tris, pH 8.0) to a final density of approximately $1 \times 10^{10}$ cells per ml. The cell suspension was mixed with one volume of 1 % molten Seaplaque LMP agarose (FMC) cooled to 40° C., and then immediately drawn into a 1 ml syringe. The syringe was sealed with parallel and placed on ice for 10 min. The cell-containing agarose plug was extruded into 10 ml of Lysis Buffer (10mM Tris pH 8.0, 50 mM NaCl, 0.1M EDTA, 1% Sarkosyl, 0.2% sodium deoxycholate, 1 mg/ml lysozyme) and incubated at 37° C. for one hour. The agarose plug was then transferred to 40 mls of ESP Buffer (1 % Sarkosyl, 1 mg/ml proteinase K, in 0.5M EDTA), and incubated at 55° C. for 16 hours. The solution was decanted and replaced with fresh ESP Buffer, and incubated at 55° C. for an additional hour. The agarose plugs were then placed in 50 mM EDTA and stored at 4° C. shipboard for the duration of the oceanographic cruise.

One slice of an agarose plug (72 µl) prepared from a sample collected off the Oregon coast was dialyzed overnight at 4° C. against 1 mL of buffer A (100 mM NaCl, 10 mM Bis Tris Propane-HCl, 100 µg/ml acetylated BSA: pH 7.0 @ 25° C.) in a 2 mL microcentrifuge tube. The solution was replaced with 250 µl of fresh buffer A containing 10 mM MgCl$_2$ and 1 mM DTT and incubated on a rocking platform for 1 hr at room temperature. The solution was then changed to 250 µl of the same buffer containing 4U of Sau3A1 (NEB), equilibrated to 37° C. in a water bath, and then incubated on a rocking platform in a 37° C. incubator for 45 min. The plug was transferred to a 1.5 ml microcentrifuge tube and incubated at 68° C. for 30 min to inactivate the enzyme and to melt the agarose. The agarose was digested and the DNA dephosphorylased using Gelase and HK-phosphatase (Epicentre), respectively, according to the manufacturer's recommendations. Protein was removed by gentle phenol/chloroform extraction and the DNA was ethanol precipitated, pelleted, and then washed with 70% ethanol. This partially digested DNA was resuspended in sterile H$_2$O to a concentration of 2.5 ng/µl for ligation to the pFOS1 vector.

PCR amplification results from several of the agarose plugs (data not shown) indicated the presence of significant amounts of archaeal DNA. Quantitative hybridization experiments using rRNA extracted from one sample, collected at 200 m of depth off the Oregon Coast, indicated that planktonic archaea in (this assemblage comprised approximately 4.7% of the total picoplankton biomass (this sample corresponds to "PACI"-200 m in Table 1 of DeLong et al., high abundance of Archaea in Antarctic marine picoplankton, *Nature*, 371:695–698, 1994). Results from archaeal-biased rDNA PCR amplification performed on agarose plug lysates confirmed the presence of relatively large amounts of archaeal DNA in this sample. Agarose plugs prepared from this picoplankton sample were chosen for subsequent fosmid library preparation. Each 1 ml agarose plug from this site contained approximately 7.5×10$^5$ cells, therefore approximately 5.4×10$^5$ cells were present in the 72 µl slice used in the preparation of the partially digested DNA.

Vector arms were prepared from pFOS1 as described (Kim et al., Stable propagation of casmid sized human DNA inserts in an F factor based vector, *Nucl. Acids Res.*, 20:10832–10835, 1992). Briefly, the plasmid was completely digested with AstII, dephosphorylated with HK phosphatase, and then digested with BamHI to generate two arms, each of which contained a cos site in the proper orientation for cloning and packaging ligated DNA between 35–45 kbp. The partially digested picoplankton DNA was ligated overnight to the PFOS1 arms in a 15 µl ligation reaction containing 25 ng each of vector and insert and 1U of T4 DNA ligase (Boehringer-Mannheim). The ligated DNA in four microliters of this reaction was in vitro packaged using the Gigapack XL packaging system (Stratagene), the fosmid particles transfected to *E. coli* strain DH10B (BRL), and the cells spread onto LB$_{cm15}$ plates. The resultant fosmid clones were picked into 96-well microliter dishes containing LB$_{cm15}$ supplemented with 7% glycerol. Recombinant fosmids, each containing ca. 40 kb of picoplankton DNA insert, yielded a library of 3.552 fosmid clones, containing approximately 1.4×10$^8$ base pairs of cloned DNA. All of the clones examined contained inserts ranging from 38 to 42 kbp. This library was stored frozen at −80° C. for later analysis.

Numerous modifications and variations of the present invention are possible in light of the above teachings; therefore, within the scope of the claims, the invention may be practiced other than as particularly described.

What is claimed is:

1. A method for identifying a desired bioactivity encoded by a genomic DNA population comprising:
    (a) obtaining a single-stranded genomic DNA population;
    (b) contacting the single-stranded DNA population of (a) with at least one DNA probe or a mixture of probes under conditions and for sufficient time to allow hybridization and to produce a double-stranded complex of probe and members of the genomic DNA population which hybridize thereto;
    (c) separating the complex from the single-stranded DNA population of (b);
    (d) releasing from the probe the members of the genomic population which had been bound to the probe;
    (e) forming double-stranded DNA from the members of the genomic population of (d);
    (f) introducing the double-stranded DNA of (e) into a suitable host cell to produce a library containing a plurality of clones containing the selected DNA; and
    (g) screening the library for clones encoding the desired activity.

2. The method of claim 1, wherein the genomic DNA population is derived from uncultivated or cultivated microorganisms.

3. The method of claim 2, wherein the uncultivated or cultivated microorganisms are isolated from an environmental sample.

4. The method of claim 3, wherein the microorganisms isolated from an environmental sample are extremophiles.

5. The method of claim 4, wherein the extremophiles are selected from the group consisting of thermophiles, hyperthermophiles, psychrophiles, halophiles, acidophiles, barophiles and psychrotrophs.

6. The method of claim 1, wherein the genomic DNA, or fragments thereof, comprise one or more operons, or portions thereof.

7. The method of claim 6, wherein the operons, or portions thereof, encodes a complete or partial metabolic pathway.

8. The method of claim 7, wherein the operons or portions thereof encoding a complete or partial metabolic pathway encodes polyketide synthases.

9. The method of claim 1, wherein the library containing a plurality of clones is selected from the group consisting of phage, plasmids, phagemids, cosmids, phosmids, viral vectors and artificial chromosomes.

10. The method of claim 1, wherein the suitable host cell is selected from the group consisting of a bacterium, fungus, plant cell, insect cell and animal cell.

11. The method of claim 1, wherein the DNA probe bound to a ligand is comprised of at least a portion of the coding region sequence of DNA for a known bioactivity.

12. The method of claim 1, wherein the ligand is selected from the group consisting of antigens or haptens, biotin or aminobiotin, sugars, enzymes, apoenzymes homopolymeric oligonucleotides and hormones.

13. The method of claim 1, wherein the binding partner for said ligand is selected from the group consisting of antibodies or specific binding fragments thereof, avidin or streptavidin, lectins, enzyme inhibitors, apoenzyme cofactors, homopolymeric oligonucleotides and hormone receptors.

14. The method of claim 1, wherein a solid phase is selected from the group consisting of a glass or polymeric surface, a packed column of polymeric beads or magnetic or paramagnetic particles.

15. The method of claim 1, wherein the library is an expression library.

16. The method of claim 15, further comprising producing a cell-free extract of the library.

17. The method of claim 15, further comprising combining the expression library extract with a host cell-free protein extract from a metabolically rich host organism.

18. The method of claim 17, wherein the host organism is Streptomyces.

19. The method of claim 17, wherein the host organism is Bacillus.

20. The method of claim 1, wherein the library is screened using nucleic acid probes.

21. The method of claim 1, wherein the genomic DNA population is derived from plant cells.

22. The method of claim 15, wherein the library is screened using antibody probes.

23. A method for preselecting a desired DNA from a genomic DNA population comprising:
(a) obtaining a single-stranded genomic DNA population;
(b) contacting the single-stranded DNA population of (a) with at least one DNA probe or a mixture of probes under conditions and for sufficient time to allow hybridization and to produce a double-stranded complex of probe and members of the genomic DNA population which hybridize thereto;
(c) contacting the double-stranded complex of (a) with a solid phase specific binding partner for said ligand so as to produce a solid phase complex;
(d) separating the solid phase complex from the single-stranded DNA population of (a);
(e) releasing the members of the genomic population which had bound to said solid phase bound probe;
(f) separating the solid phase bound probe from the members of the genomic population which had bound thereto;
(g) forming double-stranded DNA from the members of the genomic population of (e);
(h) introducing the double-stranded DNA of (g) into a suitable host cell to form a library containing a plurality of clones containing the selected DNA; and
(i) screening the library for clones encoding the desired activity.

24. The method of claim 23, wherein the genomic DNA population is derived from uncultivated or cultivated microorganisms.

25. The method of claim 24, wherein the uncultivated or cultivated microorganisms are isolated from an environmental sample.

26. The method of claim 25, wherein the microorganisms isolated from an environmental sample are extremophiles.

27. The method of claim 26, wherein the extremophiles are selected from the group consisting of thermophiles, hyperthermophiles, psychrophiles, halophiles, acidophiles, barophiles and psychrotrophs.

28. The method of claim 23, wherein the genomic DNA, or fragments thereof, comprise one or more operons, or portions thereof.

29. The method of claim 24, wherein the operons, or portions thereof, encodes a complete or partial metabolic pathway.

30. The method of claim 25, wherein the operons or portions thereof encoding a complete or partial metabolic pathway encodes polyketide synthase.

31. The method of claim 23, wherein the library containing a plurality of clones is selected from the group consisting of phage, plasmids, phagemids, cosmids, phosmids, viral vectors and artificial chromosomes.

32. The method of claim 23, wherein the a suitable host cell is selected from the group consisting of a bacterium, fungus, plant cell, insect cell and animal cell.

33. The method of claim 23, wherein the DNA probe bound to a ligand is comprised of at least a portion of the coding region sequence of DNA for a known bioactivity.

34. The method of claim 23, wherein the ligand is selected from the group consisting of antigens or haptens, biotin or aminobiotin, sugars, enzymes, apoenzymes homopolymeric oligonucleotides and hormones.

35. The method of claim 23, wherein the binding partner for said ligand is selected from the group consisting of antibodies or specific binding fragments thereof, avidin or streptavidin, lectins, enzyme inhibitors, apoenzyme cofactors, homopolymeric oligonucleotides and hormone receptors.

36. The method of claim 23, wherein a solid phase is selected from the group consisting of a glass or polymeric surface, a packed column of polymeric beads or magnetic or paramagnetic particles.

37. The method of claim 23, wherein the library is an expression library.

38. The method of claim 15, further comprising producing a cell-free extract of the library.

39. The method of claim 15, further comprising combining the expression library extract with a host cell-free protein extract from a metabolically rich host organism.

40. The method of claim 17, wherein the host organism is Streptomyces.

41. The method of claim 17, wherein the host organism is Bacillus.

42. The method of claim 1, wherein the library is screened using nucleic acid probes.

43. The method of claim 1, wherein the genomic DNA population is derived from plant cells.

44. The method of claim 23, wherein the library is screened using antibody probes.

45. The method of claim 37, further comprising producing a cell-free extract of the expression library.

46. The method of claim 45, further comprising combining the expression library extract with a cell-free protein extract from a metabolically rich host organism.

47. The method of claim 46, wherein the host organism is Streptomyces.

48. The method of claim 46, wherein the host organism is Bacillus.

49. A method for identifying a desired bioactivity or biomolecule comprising:
(a) producing one or more expression libraries derived from nucleic acid isolated from a mixed population of organisms or single isolates or a mixture thereof;
(b) combining a cell-free extract from the expression library or libraries with crude or partially purified extracts, or pure proteins from a metabolically rich cell line to form an extract mixture free from the library; and
(c) screening said mixture to identify an activity or molecule produced by the extract mixture.

50. A method for identifying a desired bioactivity or biomolecule comprising:
(a) producing one or more expression libraries containing clones having nucleic acid inserts derived from nucleic acid isolated from a mixed population of organisms or single isolates or a mixture thereof;
(b) transferring said clones into a metabolically rich cell line; and
(c) screening said cell line to identify clones having a bioactivity or biomolecule of interest.

* * * * *